United States Patent [19]

Miller et al.

[11] Patent Number: 5,259,385
[45] Date of Patent: Nov. 9, 1993

[54] APPARATUS FOR THE CANNULATION OF BLOOD VESSELS

[75] Inventors: Christopher Miller, San Jose; Ahmed Sharkawy, Mountain View, both of Calif.

[73] Assignee: Advanced Cardiovascular Systems, Inc., Santa Clara, Calif.

[21] Appl. No.: 813,123

[22] Filed: Dec. 23, 1991

[51] Int. Cl.$^5$ .............................................. A61B 12/06
[52] U.S. Cl. ............................ 128/662.04; 128/662.05
[58] Field of Search ..................... 128/662.04, 662.05, 128/662.06, 662.03

[56] References Cited

U.S. PATENT DOCUMENTS

| | | | |
|---|---|---|---|
| 4,354,500 | 10/1982 | Colley et al. | 128/662.06 X |
| 4,582,067 | 4/1986 | Silverstein et al. | 128/662.04 X |
| 4,665,925 | 5/1987 | Millar | 128/662.04 |
| 4,887,606 | 12/1989 | Yock et al. | 128/662.06 X |
| 4,991,588 | 2/1991 | Pfleuger et al. | 128/662.06 |
| 5,070,882 | 12/1991 | Bui et al. | 128/662.06 |
| 5,109,861 | 5/1992 | Walinsky et al. | 128/662.00 |

*Primary Examiner*—Francis Jaworski
*Attorney, Agent, or Firm*—Dykema Gossett

[57] ABSTRACT

An apparatus for use in cannulation of blood vessels which includes an ultrasonic flow sensing assembly. The assembly includes inner and outer elongated electrically conducting tubular members which are separated by an electrical insulator. A piezoelectric transducer capable of generating and receiving ultrasonic waves is located at the distal ends of the tubular members and is electrically connected to them. A power source is applied to the tubular members and to the piezoelectric transducer such that when a hollow needle containing the ultrasonic flow sensing assembly is advanced through tissue, emitted and detected ultrasonic waves can be employed to locate body vessels which can then be penetrated by the sharpened end of the hollow needle.

14 Claims, 2 Drawing Sheets

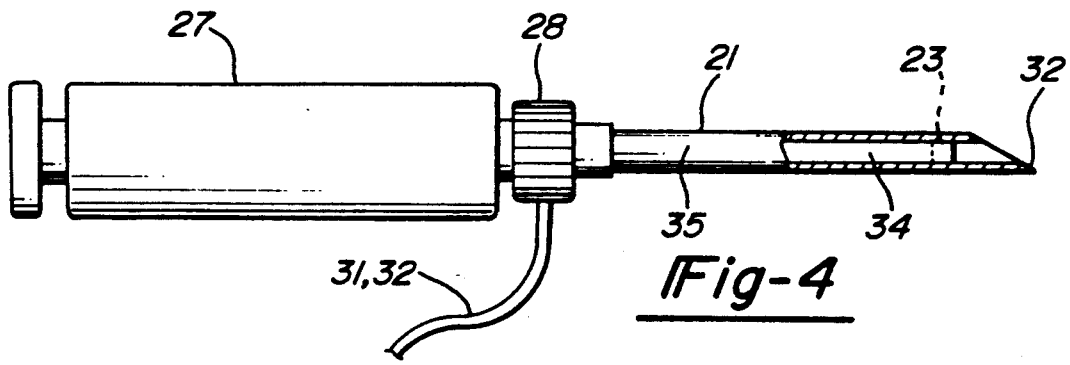
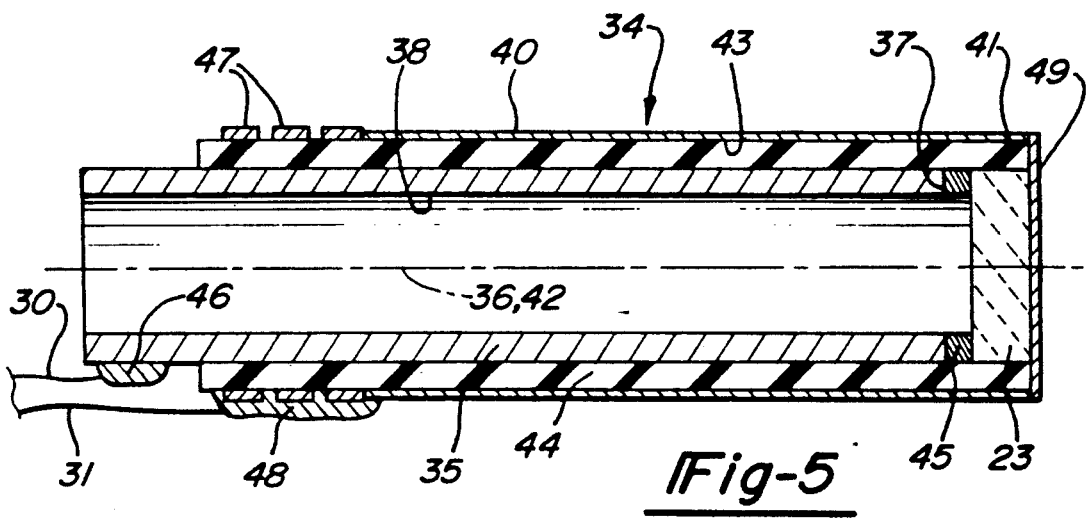
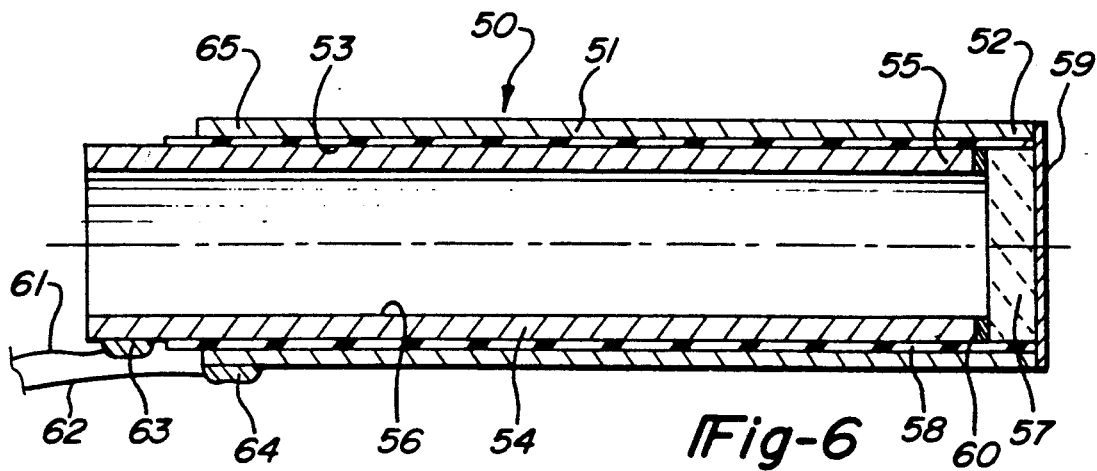

APPARATUS FOR THE CANNULATION OF BLOOD VESSELS

TECHNICAL FIELD OF THE INVENTION

The present invention relates generally to the cannulation of arteries and veins through the use of ultrasonic techniques.

BACKGROUND OF THE INVENTION

It is well established that the insertion of arterial and venous catheters for various purposes such as for angiography can be responsible for patient discomfort. Locating and penetrating arteries and veins can be especially difficult when dealing with patients who are obese or present unusual anatomy.

Arterial and venous catheters are particularly useful for cardiac catheterization and other radiologic procedures such as cerebral angiograms.

The potential utility of Doppler ultrasound for accurately guiding the needle into a vessel has been recognized. Most applications utilize the transmission of ultrasonic waves through the needle and reception of ultrasonic echoes by a separate transducer located on the body of the patient separated from the syringe and needle. Such applications obviously have limited accuracy. For example, U.S. Pat. No. 3,556,079 directed to a "Method of Puncturing a Medical Instrument Under Guidance of Ultrasound" discloses in one embodiment the placement of both the transmitting and receiving transducers in the needle and syringe. Such an embodiment, however, requires a special catheter construction and can give an erroneous signal when the needle engages the blood vessel before penetrating the vessel.

A major advance was made to this technology by virtue of U.S. Pat. No. 4,887,606 directed to "Apparatus For Use in Cannulation of Blood Vessels." This patent teaches the use of a transducer insert positioned within a hollow needle including an ultrasonic transducer at one end for transmitting and receiving ultrasonic waves through the sharpened end of the needle. Upon location and penetration of a blood vessel, the transducer insert is removable from the needle for implementation of the known Seldinger technique for placing a catheter in a blood vessel.

FIG. 1 depicts, in cross section, a device which is the subject of U.S. Pat. No. 4,887,606. In referring to FIG. 1, needle 10 is shown as having sharpened end 11 and, located therein, ultrasonic flow sensing assembly 12. The assembly 12 includes a plastic support member 13 through which a first conductor 14 extends into contact with an electrode 15 on the back surface of transducer 16. Transducer 16 is affixed to support member 13 by means of a low impedance epoxy 17 which is filled with glass microballoons (not shown). A second conductor 18 is formed on the exterior surface of support rod 40 by means of metal deposition and extends into contact with electrode 15 on the front surface of transducer 16. The conductors 14 and 18 form a coaxial cable and the outer shield conductor 18 can be grounded during use.

An insulative material 19 such as an epoxy is formed around the periphery of the transducer 16 to electrically isolate electrode 14 from conductor 18 which is in turn connected to electrode 15. Transducer 16 is positioned near the distal sharpened end 11 of needle 10 for the transmission and reception of energy through the opening in the distal sharpened end of the needle.

Although the device disclosed in U.S. Pat. No. 4,887,606, the disclosure of which is incorporated by reference herein, represents a superior apparatus for cannulation of blood vessels, such apparatus is difficult to manufacture and at times provides a device whose sensitivity is somewhat low and, ideally, could be improved upon.

The present invention provides an apparatus for the cannulation of blood vessels which is not only easier to manufacture but is also of higher sensitivity than the device shown in U.S. Pat. No. 4,887,606.

These and other advantages of the invention will become more apparent when considering the following description of the invention and the accompanying exemplary drawings.

SUMMARY OF THE INVENTION

The present invention involves an ultrasonic flow sensing assembly for use in an apparatus to be employed in the cannulation of blood vessels. The apparatus comprises a hollow needle having a longitudinal axis and sharpened distal end for penetration of tissue and a proximal end having means for detachably connecting a syringe to the needle.

The ultrasonic flow sensing assembly comprises an elongated electrically conducting first tubular member which has a longitudinal axis, a distal end and lumen extending therein. An elongated electrically conducting second tubular member is provided which has a longitudinal axis and lumen preferable coincident with the longitudinal axis and lumen of the first tubular member. The second tubular member resides substantially within the first tubular member.

An electrically insulating means such as a polymer tube is located between the first and second tubular members. A piezoelectric transducer capable of generating or receiving ultrasonic waves is located proximate the distal ends of the first and second tubular members and is electrically connected to these members. Means are further provided for connecting an electrical power source to the tubular members electrically connected to the piezoelectric transducer for the generation and reception of ultrasonic waves.

BRIEF DESCRIPTION OF THE DRAWINGS

FIG. 4 is a perspective view illustrating cannulation apparatus in accordance with the present invention.

FIG. 5 is a longitudinal cross-sectional view of an embodiment of the ultrasonic flow sensing assembly of the present invention.

FIG. 6 is a longitudinal cross-sectional view of an another embodiment of the ultrasonic flow sensing assembly of the present invention.

DETAILED DESCRIPTION OF THE INVENTION

Figure 1:
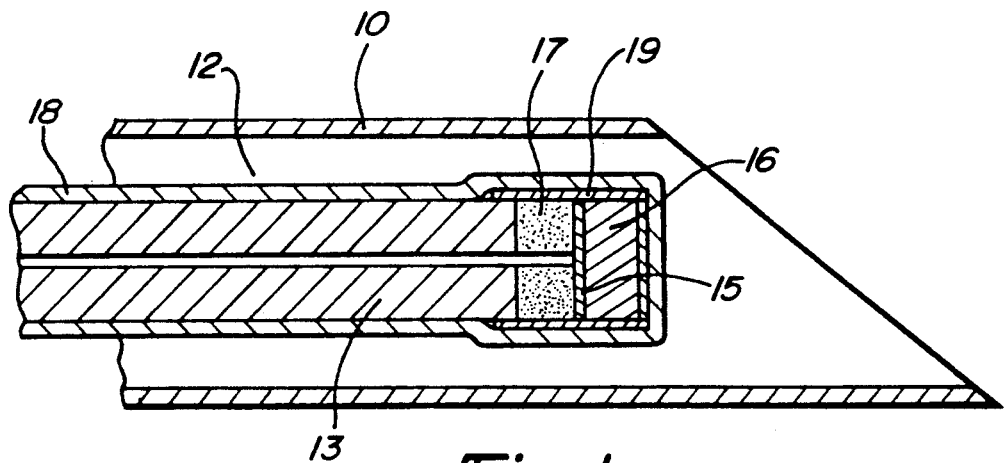
FIG. 1 represents a cross-sectional view of the prior art device depicted in U.S. Pat. No. 4,887,606.
Figure 2:
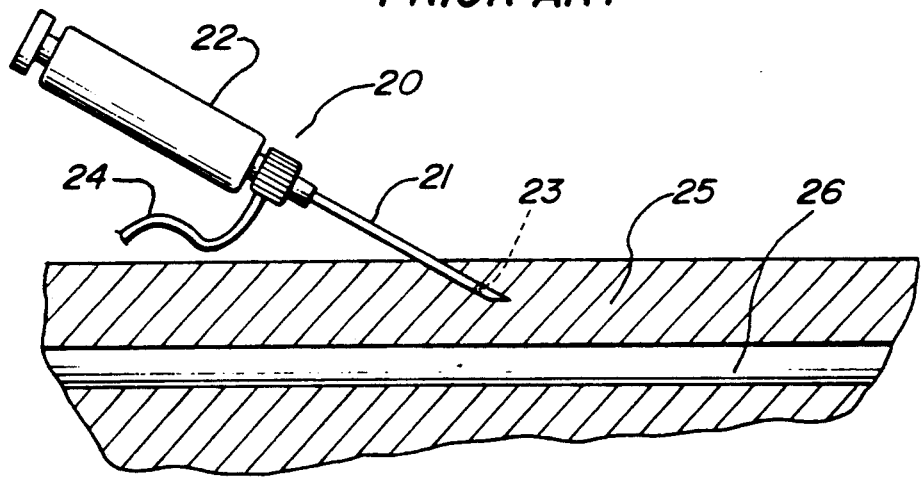
FIG. 2 is a schematic representation of a needle being inserted into tissue for cannulation of a vessel.

With reference to FIG. 2, a schematic illustration of a syringe assembly is shown generally at 20 which includes needle 21 and a container portion or syringe 22 with ultrasonic transducer means 23 within needle 21 as will be described herein below. Wire conductors 24 are electrically connected with the transducer means 23 for the transmission and reception of electrical signals. In the illustrated schematic, needle 21 is inserted through tissue 25 toward blood vessel 26.

As noted in U.S. Pat. No. 4,887,606, the insertion of arterial and venous catheters can be major source of discomfort. According to the teachings of U.S. Pat. No. 4,887,606 as well as the present invention, the piezoelectric transducer containing assembly 23 is employed to more accurately direct the needle 21 to vessel 26 and facilitate its penetration. As the needle 21 is passed through tissue 25, the sharpened distal tip of the needle is moved transversely, e.g. in a slight arc, for directing ultrasound energy transmitted through the needle to the vessel 26. The return or echo signal received by the transducer 23 is used for accurately guiding the needle 21 to the vessel 26 and provides an indication of when the needle penetrates vessel.

Figure 3:
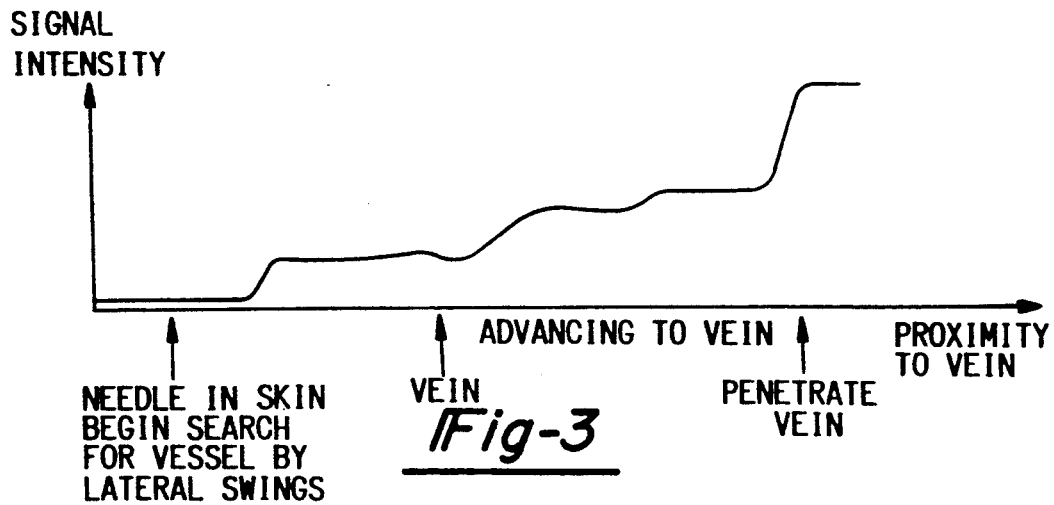
FIG. 3 is a plot of Doppler signal intensity versus distance in tissue of a needle in FIG. 2.

FIG. 3 is a plot of intensity of the Doppler signal versus depth within tissue 25. When the needle 21 is first inserted into the tissue 25, the response is small and relatively flat as indicated. Upon directing the needle toward a vein, an increased generally uniform signal is detected. As the needle is advanced toward the artery or vein, the intensity of the reflected wave increases and upon penetration of the vessel a stepped increase in the intensity of the reflected signal is indicated. Actual penetration of the vessel will be further indicated by the back flow of blood when the vessel is penetrated by maintaining a negative pressure in the needle by pulling back the syringe plunger while the needle is being advanced. A plot of intensity of the Doppler or reflected signal verses depth within the tissue with respect to the advancement toward an artery and the penetration thereof is similar to FIG. 3 except for the undulations from the heart beat. Once the vessel is penetrated, a brisk back flow of blood in the needle indicates safe penetration of the vessel and can cause a stepped increase in reflected wave intensity thereby indicating a safe location for injection of medications or for the safe passage of an introducer shaft or a guidewire into the vessel.

FIG. 4 is a perspective view of apparatus for the cannulation of blood vessels in accordance with the present invention. The apparatus includes a needle portion 21, shown in sectioned view to illustrate the ultrasonic assembly 23 therein. The needle 21 and assembly 23 are connected to syringe 27 by means of connector 28. Electrical wires 30 and 31 are interconnected through the assembly with an ultrasonic transducer 23 at one end thereof. Transducer 23 is positioned at a sharpened distal end 32 of needle 21 for the transmission and reception of ultrasonic energy through the open end of the needle.

The present invention employs an ultrasonic flow sensing assembly 34 as shown in FIG. 5 which incudes an elongated electric conducting inner tubular member 35 characterized by having a longitudinal axis 36, a distal end 37 and an inner lumen 38 extending therein.

The ultrasonic flow sensing assembly 34 also includes an elongated electrically conducting over tubular member 40 which has a distal end 41, an inner lumen 43, and a longitudinal axis 42 coincident with the longitudinal axis 36 of the inner tubular member. Elongated electrically conductive outer tubular member 40 is separated from the inner tubular member 35 by the thickness of insulating means 44 which is preferably an insulating tube formed of a polyimide. The inner tubular member 35 can be formed of stainless steel. The outer tubular member 40 of this embodiment is a layer of conductive material, such as gold, on the exterior of the insulating polyimide tube 44.

Piezoelectric transducer means 23 is capable of generating and receiving ultrasonic waves and is located at the distal ends 37 and 43 of inner and outer tubular members 35 and 40, respectively, and is electrically connected to the tubular members as shown. As a preferred embodiment, piezoelectric means 23 can be connected to tubular member 35 by an electrical conducting silver epoxy 45.

The inner lumen 38 of the inner tubular member 35 is closed by the transducer 23 which is secured to the distal end thereof. The closed inner lumen 38 forms a chamber behind the transducer which is filled with air or other gas and which greatly enhances the sensitivity of the transducer 23.

Electrical conductors 30 and 31 are shown in FIG. 5 connected to inner and outer tubular members 35 and 40, respectively. Conductor 30 is joined to the inner conductive tubular member 35 by means of a solder joint 46, whereas conductor 31 is connected to outer tube 40 via tungsten bands 47 and solder joint 48. An electrical coating 49, i.e. gold, is provided on the exterior of the transducer 23 to electrically connect the outer tubular member 40 with the transducer.

The entire assembly 34 shown in FIG. 5 can be placed within needle 21 as shown schematically in FIG. 4 for cannulation of blood vessels which can be utilized for the carrying out of a Seldinger technique. After the needle 21 is inserted and guided to a blood vessel, as described in conjunction with the discussion of FIG. 3, the blood vessel penetration is indicated by the back flow of blood through the needle past assembly 34. Once this is accomplished, assembly 34 can be removed from the needle 21 and a guidewire can be placed through the needle into the blood vessel and the needle itself then removed. Finally, prothesis can be guided into position in the blood vessel over the guidewire.

Reference is made to FIG. 6 which illustrates another preferred embodiment of an ultrasonic flow sensing assembly 50 in accordance with the invention. The assembly 50 includes an outer, electrically conductive tubular member 51 having a distal end 52 and an inner lumen 53 extending within the outer tubular member, and an inner, electrically conductive tubular member 54 having a distal end 55 and an inner lumen 56 extending within the inner tubular member. A piezoelectric transducer 57 is adjacent proximate and electrically connected to the distal ends 52 and 55 of the tubular members 51 and 54 respectively. An electrically insulating tubular member 58 is disposed between the outer and inner tubular members 51 and 54. An electrically conductive coating or layer 59 is provided on the exterior of the piezoelectric transducer 57 which extends to and electrically contacts the distal end 52 of the outer tubular member 51. An electrically conductive adhesive 60 bonds and electrically connects the distal end of the inner tubular member 54 to the backside of the piezoelectric transducer 57. Conductors 61 and 62 are secured to the proximal ends of the inner and outer tubular members 51 and 54 respectively by suitable means such as solder 63 and 64. The proximal end 65 of the outer conductive tubular member 51 is disposed a short distance from the distal end of the inner conductive tubular member 54 to provide access to the inner tubular member in order to join the conductor 66 to the inner tubular member by means of solder 63.

The operation of the ultrasonic flow sensing assembly 50 of this embodiment is essentially the same as the operation of the previously described assembly as shown in FIGS. 2-5.

Typically dimensions of the components which form the assembly 50 include an outer tubular member 51 with an OD of about 0.038 inch (0.965 mm) and an ID of about 0.034 inch (0.864 mm). The insulating tube 58 has an OD of about 0.034 inch (0.864 mm) and ID of about 0.03 inch (0.76 mm). The inner conducting tubular member 54 has an OD of about 0.03 inch (0.76 mm) and an ID of about 0.20 inch (0.51 m ). The overall length of assembly 50 is about 3.75 inches (9.53 cm) The inner and outer electrically conductive tubular members 51 and 54 may be made of stainless steel and the inner insulative tubular member 58 may be formed of polyimide. Other conducting and insulating materials may also be employed. The transverse cross sectional shape of the ultrasonic flow sensing assembly is circular to ready fit within the inner lumen of a needle and is dimensioned to leave a space between the outer surface of the assembly and the inner surface of the needle so that blood may readily flow there between. When the needle penetrates a blood vessel, blood will flow through the annular area between the assembly and the needle when a vacuum is pulled by the syringe (not shown) which is releasably secured to the proximal end of the needle.

The ultrasonic transducer is preferably formed of a lead zirconium titanate ceramic material which is sold by the Vernitron Company of Bedford, Ohio. It is sold by the designation 5H. Ceramic materials 5A is also suitable.

Various modifications and improvements may be made to the invention without departing from the scope thereof.

What is claimed is:

1. An ultrasonic flow sensing assembly comprising
   a. an elongated electrically conducting outer tubular member having a longitudinal axis, a distal end and a lumen extending therein;
   b. an elongated electrically conducting inner tubular member disposed within the outer tubular member having a longitudinal axis and lumen coincident with the longitudinal axis and lumen of said outer tubular member;
   c. electrical insulating means located between the inner and outer tubular members;
   d. a piezoelectric means capable of generating and receiving ultrasonic waves which is located proximate the distal ends of the inner and outer tubular members and being electrically connected to the tubular members, and wherein the piezoelectric means is attached to the distal ends of the inner and outer tubular members providing a closure for the inner lumens thereof; and
   e. means for connecting an electrical power source to the piezoelectric means for the generation and reception of ultrasonic waves through the tubular members.

2. The ultrasonic flow sensing assembly of claim 1 wherein the electrical insulating means is a polymer tube.

3. The ultrasonic flow sensing assembly of claim 2 wherein the polymer tube is formed of a polyimide.

4. The ultrasonic flow sensing assembly of claim 1 wherein at least one of the inner or outer tubular members is connected to piezoelectric means by means of a electrically conductive coating applied to the piezoelectric means.

5. In an apparatus for cannulation of a blood vessel comprising a hollow needle a longitudinal axis, a sharpened distal end for penetration of tissue and a syringe portion detachably connected to the proximal end of the needle, the improvement comprising an ultrasonic flow sensing assembly located within the hollow needle which includes:
   a. an elongated electrically conducting outer tubular member having a longitudinal axis, a distal end and an inner lumen extending therein;
   b. an elongated electrically conducting inner tubular member disposed within the outer tubular member having a longitudinal axis and an inner lumen coincident with the longitudinal axis and the inner lumen of the outer tubular member;
   c. electrical insulating means located between the inner and outer tubular members;
   d. a piezoelectric means capable of generating and receiving ultrasonic waves which is located proximate the distal ends of the inner and outer tubular members and being electrically connected to the tubular members; and
   e. means for connecting an electrical power source to the piezoelectric means for the generation and reception of the ultrasonic waves through the tubular members.

6. The apparatus of claim 5 wherein the inner tubular member is spaced from the hollow needle to facilitate back flow of blood when a blood vessel is penetrated.

7. The apparatus of claim 5 wherein the piezoelectric means is securely attached to the distal ends of the inner and outer tubular members providing a closure of the inner lumens thereof.

8. The apparatus of claim 5 wherein the electrical insulating means comprises a polymer tube.

9. The apparatus of claim 8 wherein the polymer tube is formed of a polyimide.

10. The apparatus of claim 5 wherein at least one of the inner or outer tubular members is connected to piezoelectric means by means of an electrically conductive coating applied to the piezoelectric transducer.

11. A method for the cannulation of blood vessels comprising:
   a) providing a hollow needle having a longitudinal axis and sharpened distal end for penetration of tissue;
   b) providing an ultrasonic flow sensing assembly within the hollow needle which includes,
      an elongated electrically conducting outer tubular member having a longitudinal axis, a distal end and a lumen extending therein,
      an elongated electrically conducting inner tubular member disposed within the outer tubular member having a longitudinal axis and lumen coincident with the longitudinal axis and lumen of the outer tubular member,
      electrical insulating means located between the inner and outer tubular members,
      piezoelectric means for generating and receiving ultrasonic waves located proximate the distal ends of the inner and outer tubular members and being electrically connected to the tubular members, and
      means for connecting an electrical power source to the piezoelectric means for the generation and reception of ultrasonic waves through the tubular members c) penetrating tissue with the sharpened distal end of the hollow needle and advancing the hollow needle and the ultrasonic flow sensing assembly through issue;

d) directing the sharpened distal end of the needle in various directions while emitting ultrasonic waves through the sharpened distal tip of the hollow needle from the piezoelectric means;

e) detecting reflected ultrasonic waves by means of the piezoelectric means; and f) determining from the detected reflected ultrasonic waves, the location of a body vessel which is to be penetrated by the sharpened distal end of the hollow needle.

12. The method of claim 11 including the step of penetrating the body vessel.

13. The method of claim 11 wherein the body vessel is a blood vessel.

14. The method of claim 13 including the step of applying a vacuum to the hollow needle by means of a syringe on the proximal end of the hollow needle after the needle penetrates the blood vessel to aspirate blood through the needle into the syringe.

* * * * *